United States Patent
Yamazaki et al.

(10) Patent No.: US 6,226,544 B1
(45) Date of Patent: May 1, 2001

(54) LIVING BODY INTERNAL ACTIVE SOURCE ESTIMATION APPARATUS

(75) Inventors: Toshimasa Yamazaki; Kenichi Kamijyo; Tomoharu Kiyuna, all of Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/096,368

(22) Filed: Jun. 12, 1998

(30) Foreign Application Priority Data

Jun. 13, 1997 (JP) .................................................. 9-156984

(51) Int. Cl.[7] .................................................. A61B 5/05
(52) U.S. Cl. .................... 600/408; 600/409; 600/524; 324/307; 324/308; 324/309; 324/200; 324/210; 324/212
(58) Field of Search ...................... 600/407, 524, 600/408, 409; 324/307, 308, 309, 200, 207.23, 210, 211, 212, 260

(56) References Cited

U.S. PATENT DOCUMENTS

| | | | |
|---|---|---|---|
| 5,730,131 | 3/1998 | Ohyu | 28/653.1 |
| 5,785,653 | 7/1998 | Kiyuna et al. | 600/408 |

FOREIGN PATENT DOCUMENTS

| | | |
|---|---|---|
| 2-309447 | 12/1990 | (JP) . |
| 3-97446 | 4/1991 | (JP) . |
| 3-277345 | 12/1991 | (JP) . |
| 3-280934 | 12/1991 | (JP) . |
| 4-319334 | 11/1992 | (JP) . |
| 5-303562 | 11/1993 | (JP) . |
| 6-319713 | 11/1994 | (JP) . |
| 7-194567 | 8/1995 | (JP) . |
| 7-204168 | 8/1995 | (JP) . |
| 8-33616 | 2/1996 | (JP) . |
| 8-77132 | 3/1996 | (JP) . |
| 8-126623 | 5/1996 | (JP) . |
| 8-131413 | 5/1996 | (JP) . |
| 8-299295 | 11/1996 | (JP) . |
| 9-91263 | 4/1997 | (JP) . |
| 9-294732 | 11/1997 | (JP) . |

OTHER PUBLICATIONS

Article—"Magnetic Source Images Determined by a Lead–Field Analysis: The Unique Minimum–Norm Least–Squares Estimation", IEEE Transactions on Biomedical Engineering, vol. 39, pp. 665–675 (1992).

Article—"Electric Dipole Tracing in the Brain by Means of the Boundary Element Method and Its Accuracy", IEEE Transactions on Biomedical Engineering, vol. BME–34, pp. 406–414 (1987).

*Primary Examiner*—Marvin M. Lateef
*Assistant Examiner*—Jeoyuh Lin
(74) *Attorney, Agent, or Firm*—Foley & Lardner

(57) ABSTRACT

Obtaining fast dipole size estimation with less influence of noise by using a regional dipole model. An artificial neural network section 30 executes regional dipole size estimation using a neural network having coupling coefficients representing coupling states among as plurality of units and thresholds thereof.

9 Claims, 7 Drawing Sheets

DIPOLE

UNIT

LIVING BODY INTERNAL ACTIVE SOURCE ESTIMATION APPARATUS

BACKGROUND OF THE INVENTION

The present invention relates to a living body internal active source estimation apparatus for estimating positions and moments of active sources in a living body on the basis of electromagnetic field distribution observed on the living body surface.

Heretofore, when estimating active sources in a living body on the basis of electromagnetic distribution observed on the living body surface, current dipoles were used in substitution for main active sources in the brain, and the positions and the moments of the dipoles were estimated. The estimation of the positions and the moments of the dipoles from the observed electromagnetic field distribution, was executed by, for instance, a method as described in the following.

An electromagnetic model of a living body is used, and it is assumed that dipoles are generated in the living body. With these dipoles, an electromagnetic field distribution, which would be recorded at an observation point placed on a surface, is calculated.

Then, denoting the calculated value of the electromagnetic field distribution at i-th observation point by $\phi_i^{(dip)}$ and an observed value obtained by actual measurement by $\phi_i^{(mes)}$, the sum of squares of the residuals r, for instance, is calculated as a residual function of these values expressed as:

$$r = \sum_i \left(\phi_i^{(mes)} - \phi_i^{(dip)}\right)^2. \quad (1)$$

If the sum of squares of the residuals r is greater than a predetermined value, the positions and moments of the dipoles are corrected by using an optimization method based on numerical analysis, typically a Marquardt method or a Simplex Method, for reducing the sum of squares of the residuals r.

When dipole positions and moments are obtained such that they reduce the sum of squares of the residuals r to be less than the predetermined value, they are executed to be a result of estimation.

The above method is described in detail in Bin He et al., "Electric Dipole Tracing in the Brain by Means of the Boundary Element Method and Its Accuracy", IEEE dTransactions on Biomedical Engineering, Vol., BME-34., No. 6, June 1978 (hereinafter referred to as Literature 1).

An estimation method based on a regional dipole source model, is carried out by assuming a relatively large number of dipoles in a living body and fixing the positions and moments of these dipoles for estimating only the size of these dipoles.

In this method, denoting the dipole size to be estimated by $q_j$, by using a matrix F which is calculated from an electromagnetic model of the living body and the positions and directions of the dipoles, the observed value $\phi_i^{(mes)}$ is expressed as:

$$\phi_i^{(mes)} = \sum_j^m F_{ij} q_j. \quad (2)$$

Usually, the number of dipoles is greater than that of observed data. Thus, it is possible to estimate dipole size qi by obtaining the generalized inverse matrix F+ of the matrix F. This estimated dipole size is given as:

$$q = F^+ \phi^{(mes)}. \quad (3)$$

The above method is detailed in J. Z. Wang et al., "Magnetic Source Image Determined by a Lead-Field Analysis: The Unique Minimum-Norm Least-Squares Estimation", IEEE Transactions on Biomedical Engineering, Vol. BME-39, No. 7, July 1992 (hereinafter referred to as Literature 2).

The above prior art techniques, however, have the following problems.

(1) In the above method for estimating the positions and the moments of dipoles, it is necessary to repeatedly carry out the calculation a large number of times. Therefore, extremely long time should be spent until obtaining the final positions and moments of dipoles. In addition, increase of the number of assumed dipoles leads to enormous time required for the estimation. Besides, since an activity at a certain point is assumed to be a dipole, it is impossible to obtain optimal solutions for an active source having certain region.

(2) In the method using a regional dipole source model, if the observed data contains even slight noise, the data corresponding to the noise is greatly reflected on the estimation result, resulting in deterioration or loss of reliability.

SUMMARY OF THE INVENTION

The present invention was made in view of the above problems inherent in the prior art, and has an object of providing a living body internal active source estimation apparatus, which permits fast dipole size estimation with less noise influence by using a regional dipole source model.

According to an aspect of the present invention, there is provided a living body internal active source estimation apparatus for estimating positions and moments of internal active sources in a living body on the basis of electromagnetic field distribution observed on the living body surface comprising: a forward problem matrix transformation means for receiving living body model data, regional dipole position/direction data and measurement position data and (calculating and providing a forward problem matrix on the basis of the input data; a coupling coefficient/threshold calculating means for receiving electromagnetic field distribution measurement data and the forward problem matrix and calculating coupling coefficients and thresholds on the basis of the electromagnetic field distribution measurement data and the forward problem matrix; an artificial neural network means for estimating sizes of regional dipoles by using an artificial neural network having coupling coefficients representing coupling states among a plurality of units and thresholds thereof; and an estimation result output means for converting unit output data from the artificial neural network means to a result of estimation and providing the result; the artificial neural network means including: a coupling coefficient memory means for storing the coupling coefficients representing the coupling states among the units; a threshold storing means for storing the thresholds of the units; a unit output storing means for storing the unit output data; and a unit output updating means for selecting units as subject of output updating, receiving the coupling coefficients provided from the coupling coefficient storing means and the unit output data provided from the unit output storing means, updating the unit output data by updating thereof and calculating network energy from the coupling coefficients and the unit output data; the unit output data being made to be the estimation result when the rate of reduction of the network energy becomes lower than a predetermined rate.

The living body internal active source estimation apparatus further comprises: a total activity calculating means for receiving the electromagnetic field distribution measurement data and calculating internal total activity in the living body on the basis of the received electromagnetic field distribution measurement data, a spatial activity restriction calculating means for receiving regional dipole position/direction data and spatial restriction data and providing a matrix restricting the regional dipole activity size on the basis of the input data, or a generalized inverse matrix calculating means for receiving the electromagnetic field distribution measurement data and a forward problem matrix provided from the forward problem matrix converting means and calculating a generalized inverse matrix on the basis of the input data.

According to another aspect of the present invention, there is provided a living body internal active source estimation method for estimating positions and moments of active sources in a living body on the basis of electromagnetic field distribution observed on the living body surface comprising steps of: calculating a forward problem matrix on the basis of living body model data, regional dipole position/direction data and measurement position data; calculating coupling coefficients and thresholds on the basis of specified data including electromagnetic field distribution measurement data and the forward problem matrix; estimating sizes of regional dipoles by using an artificial neural network having coupling coefficients representing coupling states among a plurality of units and thresholds thereof; converting unit output data from the artificial neural network means to a result of estimation; updating the unit output data and calculating network energy from the coupling coefficients and the unit output data; and determining the unit output data as the estimation result when the rate of reduction of the network energy becomes lower than a predetermined rate.

The specified data further includes internal total activity in the living body calculated on the basis of the received electromagnetic field distribution measurement data, a matrix restricting the regional dipole activity size calculated on the basis of regional current dipole position/direction data and spatial restriction data, or a generalized inverse matrix calculated on the basis of electromagnetic field distribution measurement data and a forward problem matrix.

According to other aspect of the present invention, there is provided medium storing program of living body internal active source estimation method including the foregoing steps.

According to the present invention a mutual coupling type neural network is used for optimization of a dipole size meeting two formulas. In this method of solution, an evaluation function called energy function is defined such as to express desired function and restricting conditions that are possessed by the problems to be solved.

The estimation is executed by defining the energy function such that it takes a minimum value when unit output is brought to a state that it expresses an optimum solution. The mutual coupling type neural network permits parallel processing and thus fast estimation.

In addition, it is possible to limit the total sum of dipole sizes and readily assemble such heuristic conditions as to impose size restrictions as energy function in dependence on position relationship of dipoles.

Other objects and features will be clarified from the following description with reference to attached drawings.

PREFERRED EMBODIMENTS OF THE INVENTION

Preferred embodiments of the present invention will now be described will now be described with reference to the drawings.

Figure 1:
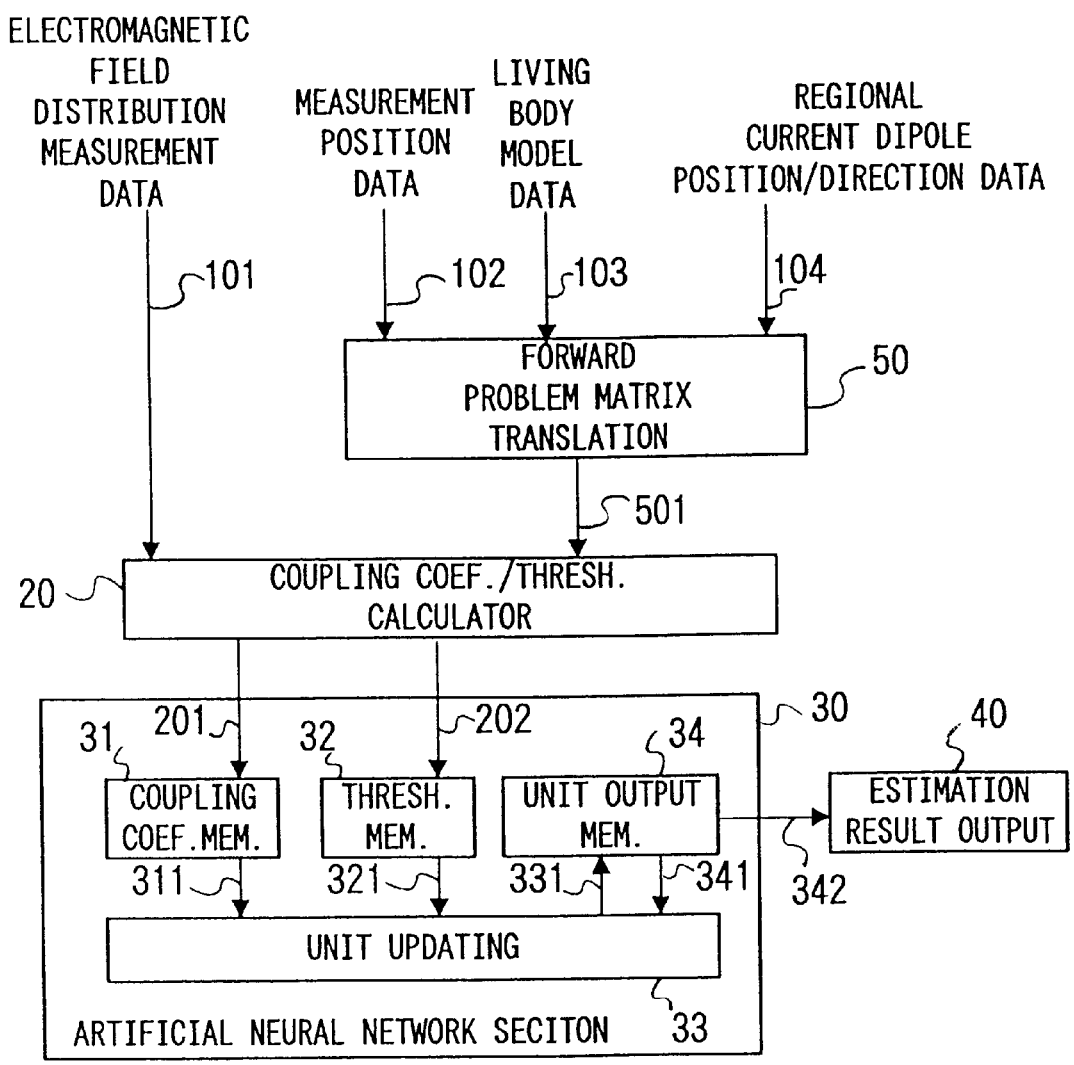
FIG. 1 is a block diagram showing the construction of a first embodiment of the living body internal active source estimation apparatus.

FIG. 1 is a block diagram showing the construction of a first embodiment of the living body internal active source estimation apparatus. The embodiment as will be described in the foregoing concerns a case of estimating the sizes of m regional current dipoles assumed in the brain from electromagnetic field distribution on the scalp, but a similar estimation method may be used in such cases when the heart or the like is the subject living body.

As electromagnetic field distribution measurement data 101 may be used brain magnetic field data obtained by measurement with a superconducting quantum interference device and electroencephalogramic data obtained with an electroencephalograph. In this embodiment, brain electromagnetic field is taken as an example. Measurement data at observation point i is denoted by $B_i^0$.

Measurement position data 102 represent the positions of a superconducting quantum interference device and electrodes used for the data observation. The position of measurement point i on the scalp is denoted by $x_i$.

Living body model data 103 represents the size, shape, laminar structure, electric conductivity, etc. of the head. Where the measurement data represents magnetic field, the living body model data 103 represents, for instance, the magnetic permeability $\mu_0$ in vacuum.

Regional current dipole position/direction data 104 represents fixed positions and directions of dipoles assumed in the brain. For example, n dipoles are set in lattice points on a surface as shown in FIG. 5, and their directions are fixed to the directions normal to the surface.

Figure 5:
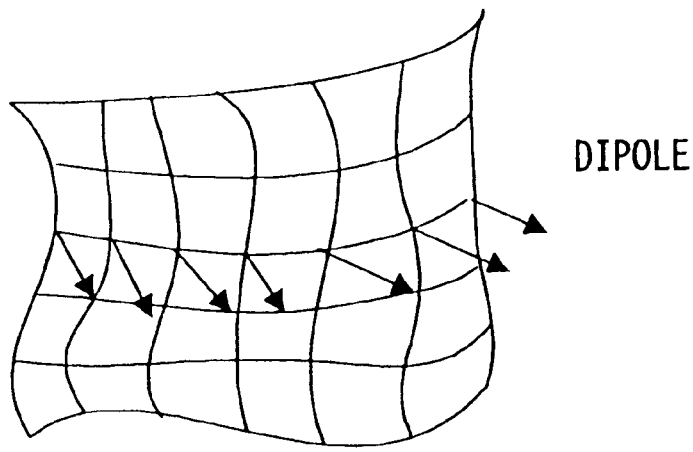
FIG. 5 is a view showing an example, in which the dipoles are regional dipoles.

FIG. 5 is a view showing an example, in which the dipoles are regional dipoles. The dipoles are shown by arrows, and dipoles in a certain row are shown schematically.

The planar arrangement of dipoles is thought to be extremely adequate from the fact that main activities in the brain take place in the cortex. In this dipole arrangement, the position and the direction of regional dipole at lattice point j are denoted by $y_j$ and $e_j$, respectively.

A forward problem matrix translator 50 receives the measurement position data 102, the living body model data 103 and the regional current dipole position/direction data 104, and provides forward problem matrix data 501 for calculating the potential on the scalp from the assumed dipoles.

The way of calculation of the forward problem matrix data $F_{ij}$ will now be described.

Denoting the component normal to a superconducting quantum interferometer observation surface at observation point i by $n_i$, a magnetic field $B_i$ at the observation point i by the regional dipoles is calculated as:

$$B_i = \frac{\mu_0}{4\pi} \int_v \frac{n_i \cdot j(y) \times (x_i - y)}{\|x_i - y\|^3} dy \quad (i = 1, 2, \ldots, n) \quad (4)$$

where j(y) is the current density at position y. For implementing the calculation process on a computer, the integral is discretely executed for transforming the formula (4) to be $$B_i = \frac{\mu_0}{4\pi} \sum_{j=1}^{m} n_i \cdot \frac{j(y_j) \times (x_i - y_j)}{\|x_i - y_j\|^3} \Delta A_j h \quad (5)$$

$$= \frac{\mu_0}{4\pi} \sum_{j=1}^{m} n_i \cdot \frac{q(y_j) \times (x_i - y_j)}{\|x_i - y_j\|^3}$$

where $\Delta A_j$ is the areas around j-th lattice point, and h is the current spread thickness.

$q(y_j) = j(y_j) \Delta A h$ is a dipole vector, and by utilizing $n_i \cdot q(y_j) \times (x - y_j) = q(y_j) \cdot (x - y_j) \times n_i$ the magnetic field can be given as:

$$B_i = \sum_{j=1}^{m} F_{ij} q_j \quad (6)$$

where $q_j$ represents the size of dipole at j-th lattice point. Thus, the forward problem matrix data 501 can be defined as:

$$F_{ij} = \frac{e_j \cdot (x_i - y_j) \times n_i}{\|x_i - y_j\|^3} \quad (7)$$

and calculated absolutely from the inputted data. Furthermore, it is possible to assemble scale factor data in the matrix for normalizing the size $q_j$ of the dipole at j-th lattice point.

As the forward problem matrix translator 50 may be used a personal computer or a workstation. Also, the translator can be realized by controlling the operation of the personal computer or the workstation with a recording medium, in which a program for realizing the above algorithm is stored.

A coupling coefficient/threshold calculator 20 receives the electromagnetic field distribution measurement data 101 and the forward problem matrix data 501, and provides coupling coefficient data 201 and threshold data 202 used in a mutual coupling type neural network.

A method for computing the coupling coefficient data 201 and the threshold data 202 will now be described.

Figure 6:
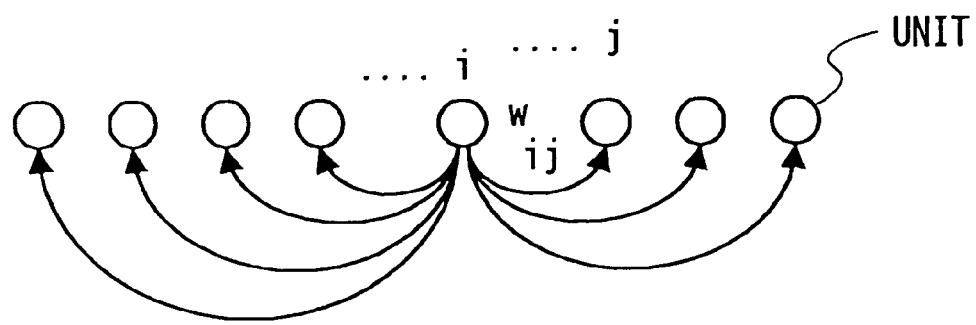
FIG. 6 is a view showing the mutual coupling type neural network.

It is assumed that the mutual coupling type neural network used according to the present invention, has a structure as shown in FIG. 6, constituted by m units each having coupling coefficients with respect to the other units.

That is, FIG. 6 shows a schematic view of an example of mutual coupling type neural network. Denoting the coupling unit of i-th unit with respect to j-th unit by $w_{ij}$, the output $v_j$ the j-th unit can be defined as:

$$v_i = f\left(\sum_j w_{ij} v_j + \theta_i\right) \quad (8)$$

where $$f(u) = \frac{1}{2}\left(1 + \tanh\left(\frac{u}{\tau_0}\right)\right) \quad (9)$$

where $\tau_0$ is a constant, and $\theta_i$ is the threshold of the i-th unit. In this case, the energy function $E_{total}$ of the network can be calculated as:

$$E_{total} = -\frac{1}{2}\left(\sum_i \sum_j w_{ij} v_i v_j - \sum_i \theta_i v_i\right) \quad (10)$$

For estimating the dipoles in the brain from the measurement data and the forward problem matrix, a dipole size $q_j$ can be estimated, which minimizes $$L_{error} = \sum_{k=1}^{n} [B_k^0 - B_k]^2 \quad (11)$$

$$= \sum_{k=1}^{n} \left[B_k^0 - \sum_{j=1}^{m} F_{kj} q_j\right]^2$$

Thus, assigning areas corresponding to the dipole size to units of the mutual coupling type neural network, makes it possible that energy Ea of the desired function is $$E_a = \sum_{k=1}^{n} \left[B_k^0 - \sum_{j=1}^{m} F_{kj} v_j\right]^2 \quad (12)$$

Assuming A to be a positive coefficient, $w_{ij}$ and $\theta_i$ can thus be determined such that $$E_{total} \equiv \frac{A}{2} E_a \quad (13)$$

From the above, the coupling coefficient $w_{ij}$ can be given as:

$$w_{ij} = \begin{cases} -A \sum_{k=1}^{n} F_{ki} F_{kj} & (i \neq j) \\ 0 & (i = j) \end{cases} \quad (14)$$

and determined absolutely from the input data. Also, the threshold of i-th unit can be given as:

$$\theta_i = A \sum_{k=1}^{n} B_k^0 F_{ki} + A(F_{ii})^2 \quad (15)$$

and determined absolutely from the input data.

As the coupling coefficient/threshold calculator 20 may be used a personal computer or a workstation. It is also possible to realize the calculator by controlling the operation of the personal computer or the workstation with a recording medium, in which a program for realizing the above algorithm is recorded. As the recording medium may be used magnetic discs, semiconductor memories and other recording media.

An artificial neural network section 30 includes a coupling coefficient: memory 31, a threshold memory 32, a unit output updating circuit 33 and a unit output memory 34, these components having the following specific functions.

The coupling coefficient memory 31 receives coupling coefficient data 201, and holds the coupling coefficient $w_{ij}$ of 1-th to j-th unit. As the coupling coefficient memory 31 may be used magnetic discs, semiconductor memories and other recording media.

The threshold memory 32 receives threshold data 202, and holds the threshold $\theta_i$ of the i-th unit. As the threshold memory 32 may be used magnetic discs, semiconductor memories and other recording media.

The unit output updating circuit 33 receives coupling coefficient data 311 and threshold data 321, and calculates the output of i-th unit as given by the formula 8 noted above. After the updating, the circuit calculates the energy of the network as given by the formula 10, and evaluates the previous difference. If the difference is less than a predetermined value, or when updating has been done by a designated number of times, the circuit stops the unit updating operation and commands feeding of updated unit output data to it.

The units, which are to be output updated, may be selected randomly or in a predetermined sequence.

As the unit output updating circuit 33 may be used a personal computer or a workstation. It is also possible to realize the circuit function by controlling the personal computer or the workstation with a recording medium, in which a program for realizing the above algorithm is recorded. As the recording medium may be used magnetic discs, semiconductor memories and other recording media.

The unit output memory 34 receives unit output updating data 331 from the unit output updating circuit 33, and updates the outputs of designated units. When the operation of the network is ended, the memory provides updated unit output data 341 held by it. As the unit output memory 34 may be used magnetic discs, semiconductor discs and other recording media.

As the neural network section 30 may be used a personal computer or a workstation. It is also possible to realize the circuit function by controlling the operation of the personal computer or the workstation with a recording medium, in which a program for realizing algorithm of the above components is stored. As the recording medium may be used magnetic discs, semiconductor memories and other recording media.

An estimation result output circuit 40 receives updated output data 431 provided from the unit output memory 34, and provides dipole size data as a result of estimation. In the case where the outputted size data is normalized data, conversion to the original scale is executed. As the estimation result output circuit 40 may be used a display or a printer.

The operation of the living body internal active source estimation apparatus having the above construction will now be described.

Figure 7:
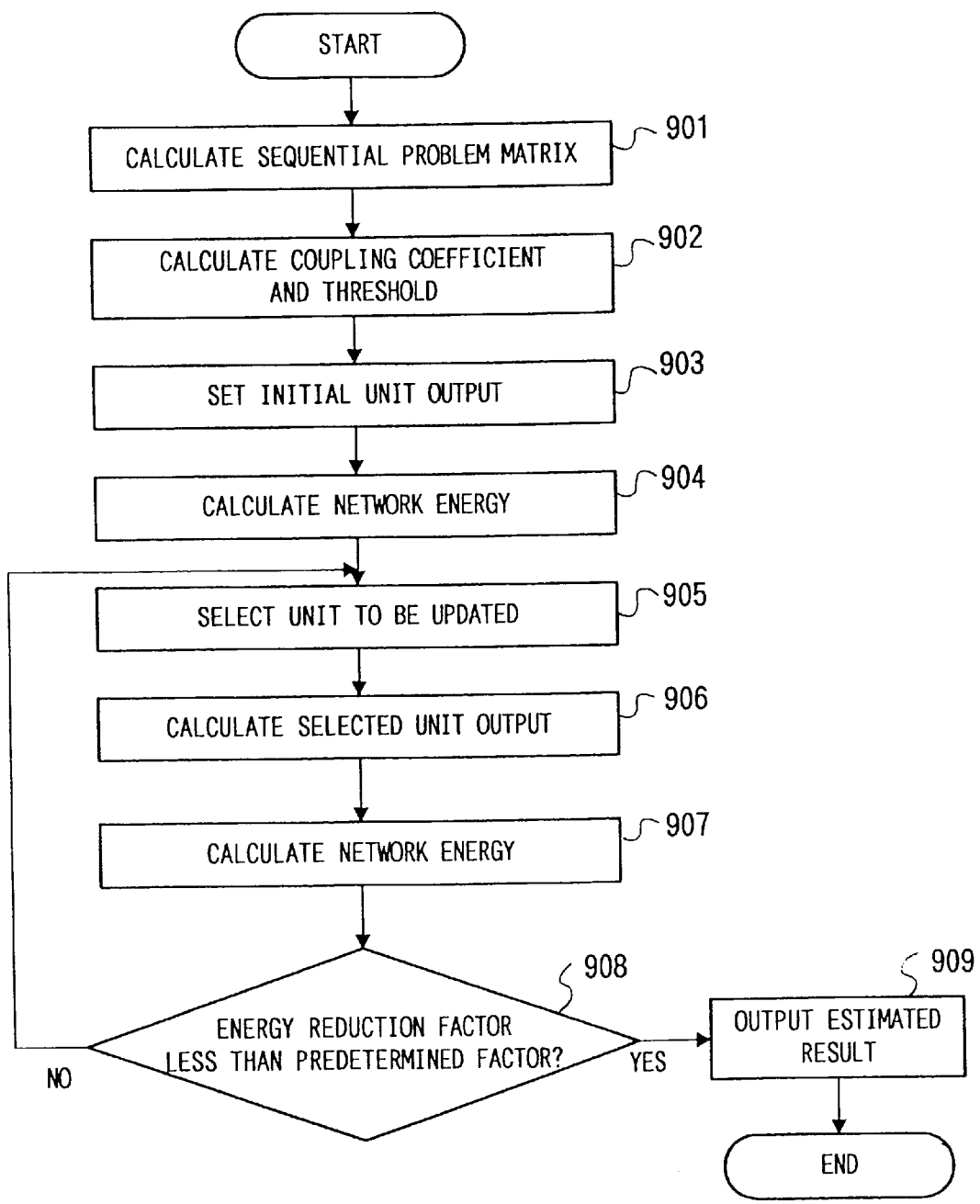
FIG. 7 is a flow chart illustrating the operation of the living body internal active source estimation apparatus shown in FIG. 1.

FIG. 7 is a flow chart illustrating the operation of the living body internal active source estimation apparatus shown in FIG. 1.

First, the forward problem matrix translator 50 receives the measurement position data 102, the living body model data 103 and the regional current dipole position/direction data 104, and calculates a regional problem matrix (step S901).

The coupling coefficient/threshold calculator 30 receives the electromagnetic field distribution measurement data 101 and the forward problem matrix data 501, calculates the coupling coefficient data 201 and the threshold data 202 in the coupling type neural network, and feeds these data to the coupling coefficient memory 31 and the threshold memory 34, respectively (step S902).

In the unit output memory 34, initial unit output data is set (step S903). Alternatively, it is possible to take values from a random number series which can take values in a certain range.

The unit output updating circuit 33 receives the coupling coefficient data 311 and the threshold data 321, and calculates the network energy (step S904). Thus, units as subject of output updating are selected (step S905). It is possible to select units randomly.

The unit output updating circuit 33 calculates output data of the selected units, and feeds these data to the unit output memory 34 (step S906).

After the output data updating, the unit output updating circuit 33 calculates the network energy (step S907). If the energy reduction factor is less than a predetermined factor, the routine goes to a step S909, while otherwise it goes to a step S905 (step S908).

Subsequently, the unit output memory 34 provides an estimation result (step S909).

When using a parallel calculator, very fast estimation can be executed by assigning the units of the mutual coupling type neural network to processor elements of the parallel calculator.

Figure 2:
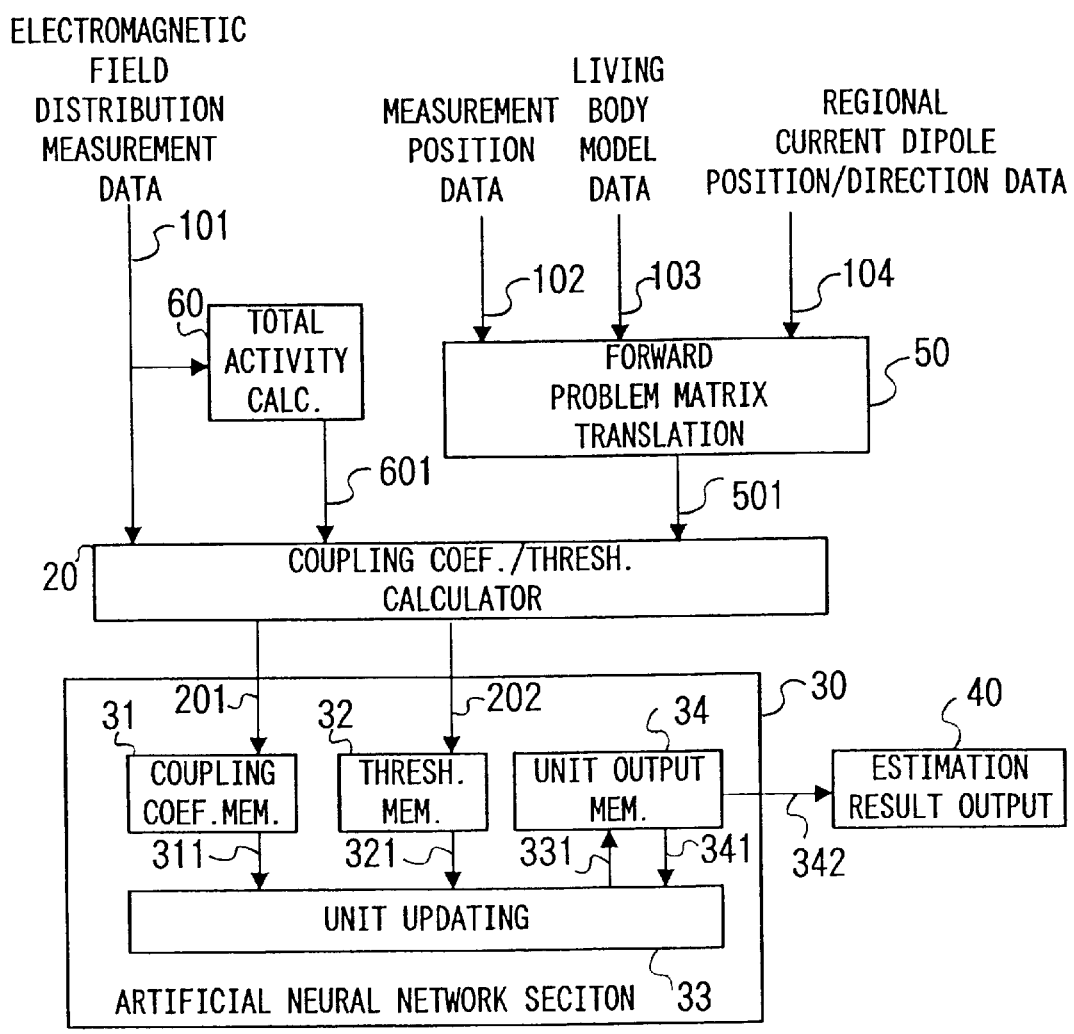
FIG. 2 is a block diagram showing the construction of a second embodiment of the living body internal active source estimation apparatus.

FIG. 2 is a block diagram showing the construction of a second embodiment of the living body internal active source estimation apparatus. In this embodiment, parts common to those shown in FIG. 1 are not described, and parts like those in FIG. 1 are designated by like reference numerals.

A total activity amount calculator 60 receives electromagnetic field distribution measurement data 101, computes the upper limit of the total activity amount of simultaneously activated units in a mutual coupling type neural network, and provides total activity amount data 601. As a method of computation may be used one, in which the mean electromagnetic field distribution measurement data is multiplied by a constant. As the total activity amount calculator 60 may be used a personal computer or a workstation. It is also possible to realize the function of the calculator by controlling the operation of the personal computer or the workstation with a recording medium, in which a program for realizing the above algorithm is recorded. As the recording medium may be used magnetic discs, semiconductor memories and other recording media.

A coupling coefficient/threshold 20 receives electromagnetic field distribution measurement data 101, forward problem matrix data 501 and total activity amount data 601, and provides coupling coefficient data 210 and threshold data 201 used in the mutual coupling type neural network. Denoting the total activity amount by M, energy $E_b$ related to the restriction on the total avtivity amount may be $$E_b = \left[\sum_i v_i - M\right]^2 \tag{16}$$

Thus, using a positive factor B, $w_{ii}$ and $\theta_i$ may be determined as:

$$E_{total} \equiv \frac{A}{2}E_a + \frac{B}{2}E_b \tag{17}$$

From the above, the coupling coefficient may be given as:

$$w_{ij} = -A\sum_{k=1}^{n} F_{ki}F_{kj} - B \tag{18}$$

and determined absolutely from input data. Also, the threshold in i-th unit may be given as:

$$\theta_i = A\sum_{k=1}^{n} B_k^0 F_{ki} + BM \tag{19}$$

and determined absolutely from input data.

By using the above apparatus, it is possible to restrict the total activation amount and suppress activation of unnecessary units.

Figure 3:
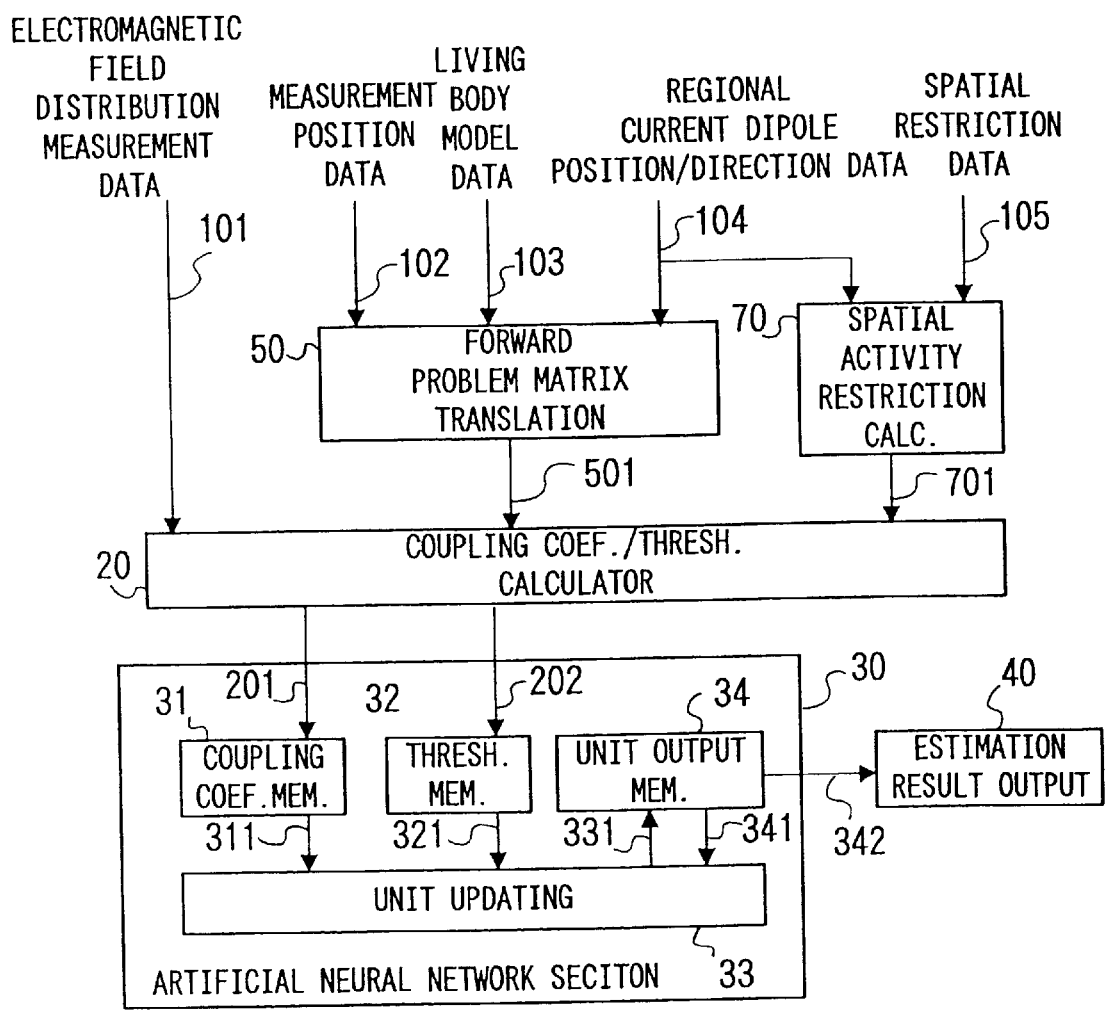
FIG. 3 is a block diagram showing the construction of a third embodiment of the living body internal active source estimation apparatus.

FIG. 3 is a block diagram showing the construction of a third embodiment of the living body internal active source estimation apparatus according to the present invention. In this embodiment, parts common to those shown in FIG. 1 are not described, and parts like those in FIG. 1 are designated by like reference numerals.

Figure 8:
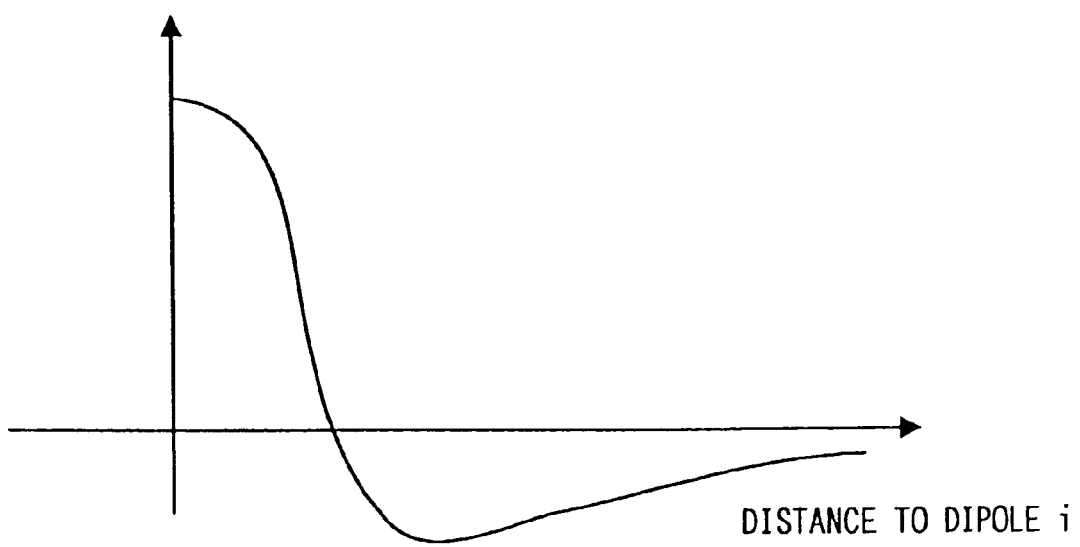
FIG. 8 is a graph showing an example of function representing the relations of the i-th dipoles to the other dipoles on the basis of the distances therefrom.

Denoting the relation between i-th and j-th dipoles by $r_{ij}$, as spatial restriction data 105 may be used a relation matrix $r_{ij}^{(1)}$ in which i-th dipole has Mexican hat type relations to the other dipoles on the basis of the distances therefrom, as shown in FIG. 8.

FIG. 8 is a graph showing an example of function representing the relations of the i-th dipoles to the other dipoles on the basis of the distances therefrom.

It is also possible to use a relation matrix $r_{ij}^{(2)}$ in which $h_1$-th dipole is neurophysiologically related $h_2$-th dipole as expressed as:

$$r_{ij}^{(2)} = \begin{cases} 1 & i = j = h_1, h_2 \\ 0 & \text{otherwise} \end{cases} \quad (20)$$

A spatial activity restriction calculator 70 receives regional current dipole position/direction data 104 and spatial restriction data 105, and it controls activation in the neighborhood of the mutual coupling type neural network by taking the spatial position relation of regional dipoles to one another into considerations and also calculates and provides spatial activity restriction matrix data 701 on the basis of neurophysiological intelligence such as to promote activation of highly related dipoles by one another.

Denoting the spatial activity restriction matrix of i-th to j-th dipole by $S_{ij}$, it is possible to compute the spatial activity restriction matrix 701 as:

$$S_{ij} = \sum_k a_k r_{ij}^{(k)} \quad (21)$$

where $a_k$ is a constant.

As the spatial activity restriction calculator 70 may be used a personal computer or a workstation. It is also possible to realize the function of the calculator by controlling the operation of the personal computer or the workstation with a recording medium, in which a program for realizing the algorithm is stored. As the recording medium may be used magnetic discs, semiconductor memories and other recording media.

A coupling coefficient/threshold calculator 20 receives electromagnetic field distribution measurement data 101, forward problem matrix data 501 and spatial activity restriction matrix data 701, and provides coupling coefficient data 201 and threshold data 202 used in the mutual coupling the neural network.

As energy $E_c$ related to spatial activity restriction may be used one given as:

$$E_c = -\sum_i \sum_j s_{ij} v_i v_j \quad (22)$$

Thus, by using a positive coefficient C, $w_{ij}$ may be $$E_{total} \equiv \frac{A}{2} E_a + \frac{C}{2} E_c \quad (23)$$

determined as:

From the above, the coupling coefficient may be given as:

$$w_{ij} = -A \sum_{k=1}^{n} F_{ki} F_{kj} + C s_{ij} \quad (24)$$

and determined absolutely from input data.

By using the above apparatus, it is possible to control the neighborhood activation and promote activation of highly related dipoles to one another on the basis of physiological finding.

Figure 4:
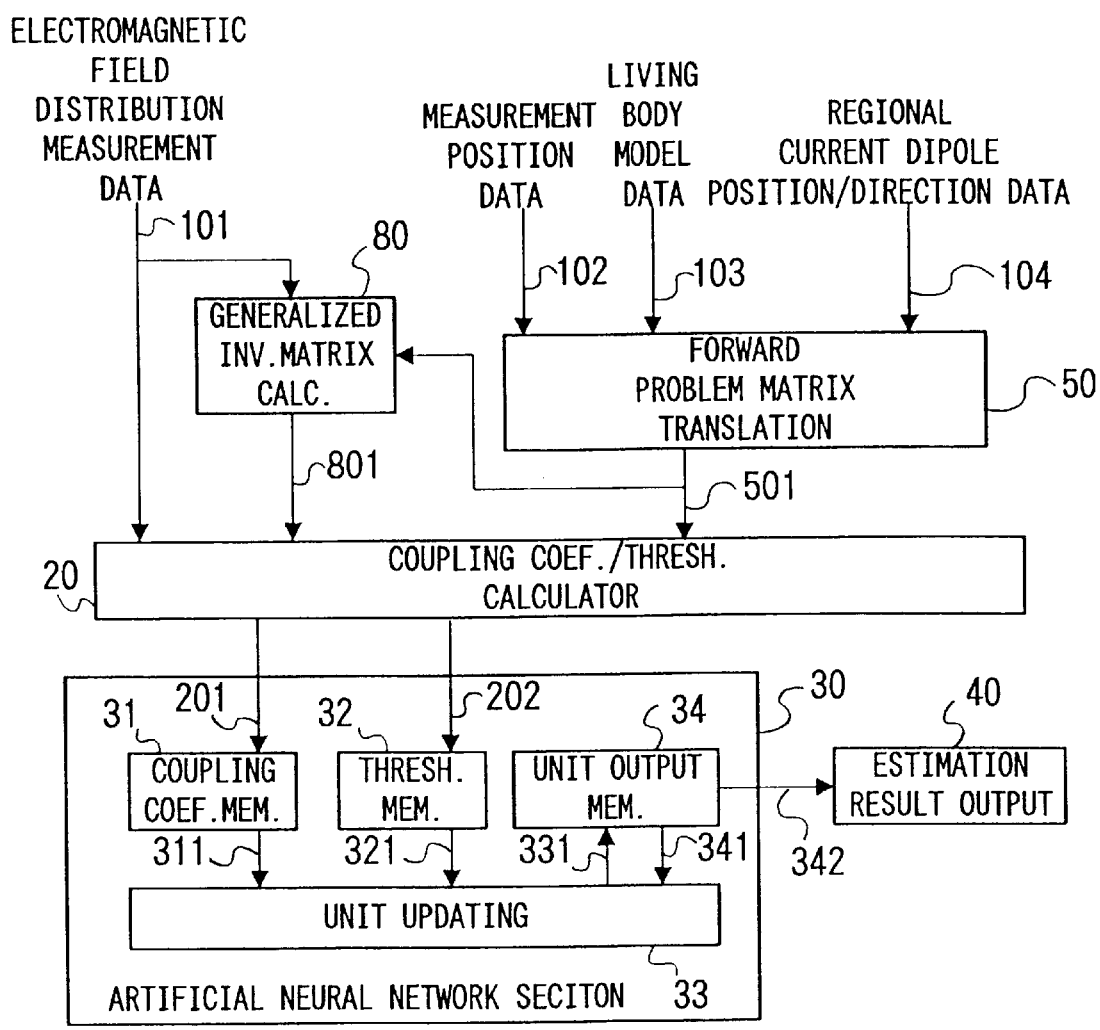
FIG. 4 is a block diagram showing the construction of a fourth embodiment of the living body internal active source estimation apparatus.

FIG. 4 is a block diagram showing the construction of a fourth embodiment of the living body internal active position estimation apparatus according to the present invention. In this embodiment, parts common to those shown in FIG. 1 are not described, and parts like those shown in FIG. 1 are designated by like reference numerals.

A generalized, inverse matrix calculator 80 receives forward problem matrix data 501, and computes the generalized inverse matrix of forward problem matrix. Also, the circuit provides estimation data 801 based on the generalized inverse matrix from electromagnetic field distribution measurement data 101. The generalized inverse matrix may be obtained from the forward problem matrix as a well-known solution utilizing the generalized inverse matrix of Moore-Penrose. The Moore-Penrose generalized inverse matrix utilizes a unique value disassembling of forward problem matrix F given as:

$$F = UAV^T \quad (25)$$

$$= (u_1, \ldots, u_n) \begin{pmatrix} \lambda_1 & & & & 0 \\ & \ddots & & & \\ & & \lambda_r & & \\ & & & 0 & \\ 0 & & & & \ddots \\ & & & & & 0 \end{pmatrix} (v_1^T, \ldots, v_m^T)^T \quad (26)$$

where $u_i$ and $v_i$ are row vectors representing i-th row of matrixes U and V, respectively, and r represents rank of the matrices F. Using the result of the unique value disassembling, the generalized inverse matrix F+of the matrix is given as:

$$F^+ = \sum_{i=1}^{r} \lambda_i v_i u_i^T \quad (27)$$

Using this generalized inverse matrix, the estimation value $\hat{q}_j$ based on the generalized inverse matrix can be obtained as:

$$\hat{q} = F^+ B^0 = \sum_{i=1}^{r} \frac{u_i^T \cdot B^0}{\lambda_i} v_i \quad (28)$$

As the generalized inverse matrix computer 80 may be used a personal computer or a workstation. It is also possible to realize the function of the calculator by controlling the operation of a personal computer or a workstation with a recording medium, in which a program for realizing the above algorithm is recorded. As the recording medium may be used magnetic discs, semiconductor memories and other recording media.

A coupling coefficient/threshold calculator 20 receives electromagnetic field distribution measurement data 101, forward problem matrix data 501 and estimation data 801 based on the generalized inverse matrix, and provides coupling coefficient data 201 and threshold data 202 used in the mutual coupling type neural network.

As energy $E_d$ related to the estimation using the generalized inverse matrix may be used one given as:

$$E_d = \sum_i [v_i - \hat{q}_i]^2 \qquad (29)$$

Thus, denoting a positive coefficient D, $w_{ij}$ and $\theta_i$ may be determined as:

$$E_{total} = \frac{A}{2} E_a + \frac{D}{2} E_d \qquad (30)$$

From the above, the coupling coefficient can be given as:

$$w_{ij} = -A \sum_{k=1}^{n} F_{ki} F_{kj} - D \qquad (31)$$

and determined absolutely from input data. Also, the threshold of i-th unit can be given as:

$$\theta_i = A \sum_{k=1}^{n} B_k^0 F_{ki} + D \hat{q}_i \qquad (32)$$

and determined absolutely from input data.

When the measurement data contains noise, the estimation data based on the generalized inverse matrix would contain erroneous values. These erroneous values may be corrected by using the above apparatus.

As has been described in the foregoing, according to the present invention by using a mutual coupling type neural network for optimization, a framework readily permitting parallel calculation can be obtained to obtain fast parallel operation. In addition, it is possible to deal with various restricting conditions all at once and thus suppress influence of noise by incorporating physiological finding or the like.

Thus, by utilizing the mutual coupling type neural network and incorporating the total activity amount restriction and spatial activity restriction, it is possible to obtain dipole size estimation with less noise influence.

Changes in construction will occur to those skilled in the art and various apparently different modifications and embodiments may be executed without departing from the scope of the present invention. The matter set forth in the foregoing description and accompanying drawings is offered by way of illustration only. It is therefore intended that the foregoing description be regarded as illustrative rather than limiting.

What is claimed is:

1. A living body internal activity position estimation apparatus for estimating positions and moments of active sources in a living body on the basis of electromagnetic field distribution observed on the living body surface, comprising:

a forward problem translation means for receiving living body model data, for receiving dipole position/direction data, and for receiving measurement position data, the forward problem matrix translation means calculating and providing a forward problem matrix on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data and the forward problem matrix;

an artificial neural network means for estimating sizes of regional dipoles by using a neural network having coupling coefficients representing coupling states among a plurality of units and thresholds thereof; and an estimation result output means for converting unit output data from the neural network means to a result of estimation and providing the result;

the neural network means including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data; and a spatial activity restriction calculating means for receiving regional current dipole position/direction data and spatial restriction data, the spatial activity restriction calculating means providing a matrix restricting the regional dipole activity on the basis of the received data, wherein the output data is output as the estimation result when a rate of reduction of the network energy becomes lower than a predetermined rate.

2. A living body internal active source estimation apparatus for estimating positions and moments of active sources in a living body on the basis of electromagnetic field distribution observed on the living body surface, comprising:

a forward problem translation means for receiving living body model data, for receiving dipole position/direction data, and for receiving measurement position data, the forward problem matrix translation means calculating and providing a forward problem matrix on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data and the forward problem matrix;

an artificial neural network means for estimating sizes of regional dipoles by using a neural network having coupling coefficients representing coupling states among a plurality of units and thresholds thereof; and an estimation result output means for converting unit output data from the neural network means to a result of estimation and providing the result;

the neural network means including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data; and a generalized inverse matrix calculating means for receiving the electromagnetic field distribution measurement data and a forward problem matrix provided from the forward problem matrix converting means, the generalized inverse matrix calculating means calculating a generalized inverse matrix on the basis of the received data, wherein the output data is output as the estimation result when a rate of reduction of the network energy becomes lower than a predetermined rate.

3. A living body internal active source estimation apparatus for estimating positions and moments of active sources in a living body on the basis of electromagnetic field distribution observed on the living body surface, comprising:

a forward problem translation means for receiving living body model data, for receiving dipole position/direction data, and for receiving measurement position data, the forward problem matrix translation means calculating and providing a forward problem matrix on the basis of the received data;

a spatial activity restriction current dipole means for receiving regional current dipole position/direction data and for receiving spatial restriction data, the spatial activity restriction current dipole means providing a matrix restricting the regional dipole activity size on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data and the forward problem matrix;

a neural network means for estimating sizes of regional dipoles by using a neural network having coupling coefficients representing coupling states among a plurality of units and thresholds thereof; and an estimation result output means for converting unit output data from the neural network means to a result of estimation and providing the result;

the neural network means; including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data;

wherein the output data is output as the estimation result when a rate of reduction of the network energy becomes lower than a predetermined rate.

4. A living body internal active source estimation apparatus for estimating positions and moments of active sources in a living body on the basis of electromagnetic field distribution observed on the living body surfaces comprising:

a forward problem translation means for receiving living body model data, for receiving dipole position/direction data, and for receiving measurement position data, the forward problem matrix translation means calculating and providing a forward problem matrix on the basis of the received data;

a generalized inverse matrix calculating means for receiving the electromagnetic field distribution measurement data and a forward problem matrix provided from the forward problem matrix converting means, the coupling coefficient/threshold calculating means calculating a generalized inverse matrix on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data, and the forward problem matrix and the generalized inverse matrix;

an artificial neural network means for estimating sizes of regional dipoles by using a neural network having coupling coefficients representing coupling states among a plurality of units and thresholds thereof; and an estimation result output means for converting unit output data from the neural network means to a result of estimation and providing the result; and an estimation result output means for converting unit output data from the neural network means to a result of estimation and providing the result;

the neural network means including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data;

wherein the output data is output as the estimation result when a rate of reduction of the network energy becomes lower than a predetermined rate.

5. A living body internal active source estimation method for estimating positions and moments of active sources in a living body on the basis of electromagnetic field distribution observed on the living body surface, comprising the steps of:

calculating a forward problem matrix on the basis of living body model data, regional dipole position/direction data and measurement position data;

calculating coupling coefficients and thresholds on the basis of specified data including electromagnetic field distribution measurement data and the forward problem matrix;

estimating sizes of regional dipoles by using a neural network having coupling coefficients representing coupling states among a plurality of units and thresholds thereof;

converting unit output data from the neural network to a result of estimation;

updating the unit output data and calculating network energy from the coupling coefficients and the unit output data; and determining the unit output data as the estimation result when a rate of reduction of the network energy becomes lower than a predetermined rate, wherein the specified data further includes internal total activity in the living body calculated on the basis of the received electromagnetic field distribution measurement data, a matrix restricting the regional dipole activity size calculated on the basis of regional current dipole position/direction data and spatial restriction data, or a generalized inverse matrix calculated on the basis of electromagnetic field distribution measurement data and a forward problem matrix.

6. A living body internal activity position estimation apparatus for estimating positions and moments of active sources in a living body on the basis of electromagnetic field distribution observed on the living body surface, comprising:

a forward problem translation means for receiving living body model data, for receiving dipole position/direction data, and for receiving measurement position data, the forward problem matrix translation means calculating and providing a forward problem matrix on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data and the forward problem matrix;

an artificial neural network means for estimating sizes of regional dipoles by using a neural network having coupling coefficients representing coupling states among a plurality of units and thresholds thereof; and an estimation result output means for converting unit output data from the neural network means to a result of estimation and providing the result;

the neural network means including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data;

a total activity calculating means for receiving the electromagnetic field distribution measurement data and calculating internal total activity in the living body on the basis of the received electromagnetic field distribution measurement data; and a spatial activity restriction calculating means for receiving regional current dipole position/direction data and spatial restriction data, the spatial activity restriction calculating means providing a matrix restricting the regional dipole activity on the basis of the received data, wherein the output data is output as the estimation result when a rate of reduction of the network energy becomes lower than a predetermined rate.

7. A living body internal activity position estimation apparatus for estimating positions and moments of active sources in a living body on the basis of electromagnetic field distribution observed on the living body surface, comprising:

a forward problem translation means for receiving living body model data, for receiving dipole position/direction data, and for receiving measurement position data, the forward problem matrix translation means calculating and providing a forward problem matrix on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data and the forward problem matrix;

an artificial neural network means for estimating sizes of regional dipoles by using a neural network having coupling coefficients representing coupling states among a plurality of units and thresholds thereof; and an estimation result output means for converting unit output data from the neural network means to a result of estimation and providing the result;

the neural network means including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data;

a total activity calculating means for receiving the electromagnetic field distribution measurement data and calculating internal total activity in the living body on the basis of the received electromagnetic field distribution measurement data; and a generalized inverse matrix calculating means for receiving the electromagnetic field distribution, measurement data and a forward problem matrix provided from the forward problem matrix converting means, the generalized inverse matrix calculating means calculating a generalized inverse matrix on the basis of the received data, wherein the output data is output as the estimation result when a rate of reduction of the network energy becomes lower than a predetermined rate.

8. A living body internal active source estimation apparatus for estimating positions and moments of active sources in a living body on the basis of electromagnetic field distribution observed on the living body surface, comprising a forward problem translation means for receiving living body model data, for receiving dipole position/direction data, and for receiving measurement position data, the forward problem matrix translation means calculating and providing a forward problem matrix on the basis of the received data;

a coupling coefficient/threshold calculating means for receiving electromagnetic field distribution measurement data and the forward problem matrix, the coupling coefficient/threshold calculating means calculating coupling coefficients and thresholds on the basis of the electromagnetic field distribution measurement data and the forward problem matrix;

an artificial neural network means for estimating sizes of regional dipoles by using a neural network having coupling coefficients representing coupling states among a plurality of units and thresholds thereof; and an estimation result output means for converting unit output data from the neural network means to a result of estimation and providing the result;

the neural network means including:

a coupling coefficient storing means for storing the coupling coefficients representing the coupling states among the units;

a threshold storing means for storing the thresholds of the units;

a unit output storing means for storing the unit output data;

a unit output updating means for selecting units as subject of output updating, receiving the coupling coefficients provided from the coupling coefficient storing means and the unit output data provided from the unit output storing means, updating the unit output data and calculating network energy from the coupling coefficients and the unit output data;

a total activity calculating means for receiving the electromagnetic field distribution measurement data and calculating internal total activity in the living body on the basis of the received electromagnetic field distribution measurement data; and a generalized inverse matrix calculating means for receiving the electromagnetic field distribution measurement data and a forward problem matrix provided from the forward problem matrix converting means, the generalized inverse matrix calculating means calculating a generalized inverse matrix on the basis of the received data, wherein the output data is output as the estimation result when a rate of reduction of the network energy becomes lower than a predetermined rate.

9. Medium storing program of living body internal active source estimation method including steps as set forth in claim 5.

* * * * *